US00PP14715P2

(12) United States Plant Patent
Wigchert

(10) Patent No.: US PP14,715 P2
(45) Date of Patent: Apr. 20, 2004

(54) DELPHINIUM PLANT NAMED 'CORAL SUNSET'

(50) Latin Name: *Delphinium elatum*
Varietal Denomination: Coral Sunset

(75) Inventor: Nico Wigchert, Noordwijkerhout (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 10/437,937

(22) Filed: May 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Delphinium plant named 'Coral Sunset', characterized by its upright plant habit; freely flowering habit; and double light red-colored flowers.

2 Drawing Sheets

Botanical classification/cultivar designation: *Delphinium elatum* cultivar Coral Sunset.

BACKGROUND OF THE INVENTION

The present Invention relates to a new and distinct cultivar of Delphinium plant, botanically known as *Delphinium elatum*, and hereinafter referred to by the name 'Coral Sunset'.

The new Delphinium was discovered by the Inventor in 1999 in a controlled environment in Noordwijkerhout, The Netherlands, as a naturally-occurring whole plant mutation of the *Delphinium elatum* cultivar Princess Caroline, not patented. The new Delphinium was selected by the Inventor on the basis of its unique light red-colored flowers.

Asexual reproduction of the new Delphinium by cuttings in a controlled environment in Noordwijkerhout, The Netherlands, since 2000, has shown that the unique features of this new Delphinium are stable and reproduced true to type in successive generations.

SUMMARY OF THE INVENTION

Plants of the cultivar Coral Sunset have not been observed under all possible environmental conditions. The phenotype may vary somewhat with variations in environment such as temperature and light intensity without, however, any variance in genotype.

The following traits have been repeatedly observed and are determined to be the unique characteristics of 'Coral Sunset'. These characteristics in combination distinguish 'Coral Sunset' as a new and distinct cultivar:

1. Upright plant habit.
2. Freely flowering habit.
3. Double light red-colored flowers.

Plants of the cultivar Coral Sunset differ from the parent cultivar, Princess Caroline and other Delphinium cultivars known to the Inventor in its unique flower coloration. In addition, compared to plants of the cultivar Princess Caroline, plants of the new Delphinium are shorter than plants of the cultivar Princess Caroline.

BRIEF DESCRIPTION OF THE PHOTOGRAPHS

The accompanying colored photographs illustrate the overall appearance of the new Delphinium, showing the colors as true as it is reasonably possible to obtain in colored reproductions of this type. Colors in the photographs may differ slightly from the color values cited in the detailed botanical description which accurately describe the colors of the new Delphinium.

The photograph on the first sheet comprises a side perspective view of a typical flowering plant of 'Coral Sunset' grown in a container.

The photograph at the top of the second sheet is a close-up view of typical flowers of 'Coral Sunset'.

The photograph at the bottom of the second sheet is a close-up view of the upper surface of a typical leaf of 'Coral Sunset'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description were about one year old and grown under outdoor field conditions which closely approximate commercial production conditions in Hillegom, The Netherlands. During the production of the plants, day temperatures ranged from 15 to 27° C. and night temperatures ranged from 7 to 14° C. The photographs and description were taken in September, 2002.

Botanical classification: *Delphinium elatum* cultivar Coral Sunset.

Parentage: Naturally-occurring whole plant mutation of the *Delphinium elatum* cultivar Princess Caroline, not patented.

Propagation:

*Type cutting.*—By cuttings.

*Time to initiate roots.*—About 14 days at 14° C.

*Time to produce a rooted cutting.*—About 40 days at 20° C.

*Root description.*—Fine.

Plant description:

*Form.*—Upright perennial flowering plant with double flowers arranged on erect racemes. During a growing season, about four flower racemes develop per plant; moderately vigorous growth habit.

*Plant height.*—About 95 cm.

*Plant diameter.*—About 35 cm.

*Primary flowering stems.*—Length: About 95 cm. Diameter: About 4 mm. Internode length: About 2.9 cm. Strength: Strong. Texture: Smooth; slightly glaucous. Color: 143A to 143B.

*Foliage description.*—Arrangement: Rosette at the base and alternate along flowering stems; simple. Length: About 14.7 cm. Width: About 21.3 cm. Shape: Deeply palmate to pedately-lobed. Apex: Acute. Base: Hastate. Margin: Incised to laciniate. Texture: Upper surface: Glabrous. Lower surface: Sparse pubescence at veins and margins. Venation pattern: Laciniate. Color: Young foliage, upper surface: Between 141A and 143A. Young foliage, lower surface: 138B. Fully expanded foliage, upper surface: 139A. Fully expanded foliage, lower surface: 138B. Venation, upper surface: 143A. Venation, lower surface: 143B. Petiole: Length: About 8.6 cm. Diameter: About 3.5 mm by 5 mm. Texture: Smooth. Color: 143B.

Flower description:

*Appearance.*—Double flowers arranged in terminal racemes; flowers zygomorphic. Flowers face mostly outward. Flowers not persistent.

*Quantity of flowers.*—Freely flowering. Primary flowering stem, about 75 flowers; secondary flowering stems, about 25 flowers each.

*Natural flowering season.*—Flowering continuous from July through September in The Netherlands.

*Fragrance.*—None detected.

*Flower longevity on the plant.*—About ten days.

*Flower longevity as a cut flower.*—At least ten days.

*Inflorescence size.*—Length: About 52 cm. Diameter: About 16 cm.

*Flower size.*—Diameter: About 5.7 cm. Depth, excluding spur: About 3.8 cm.

*Flower buds.*—Length, including spur: About 3.2 cm. Diameter: About 9 mm. Shape: Ovoid. Color: Upper surface, 22B; lower surface, 145C; towards the apex, 143A to 143B.

*Petals/petaloids.*—Appearance/arrangement: About four petals and about 22 petaloids per flower arranged in multiple whorls. Length: Petals: About 2.6 cm. Petaloids, largest: About 2.4 cm. Width: Petals: About 1.4 cm. Petaloids, largest: About 1.3 cm. Shape: Petals: Obovate to oblanceolate. Petaloids: Outermost petaloids: Obovate to oblanceolate. Innermost petaloids: Oblanceolate to narrowly oblanceolate. Apex, petals and petaloids: Obtuse. Margin, petals and petaloids: Entire. Texture, petals and petaloids, upper and lower surfaces: Smooth, glabrous. Color, petals and petaloids: When opening, upper surface: 38B; towards the base, 145B to 145D. When opening, lower surface: 38B; towards the base, 145A to 145C. Fully opened, upper surface: 51B to 51C; towards the base, 145D. Fully opened, lower surface: 51B; towards the base, 145B to 145C.

*Sepals.*—Quantity/arrangement: Five per flower; rotate; one with a spur. Length: About 2.4 cm. Width: About 1.6 cm. Shape: Obovate to elliptic. Apex: Acute to obtuse. Base: Cuneate. Margin: Entire. Color: When opening, upper surface: 38B; spot at the apex, 144B to 144C. When opening, lower surface: 38B; spot at the apex, 143A to 143C. Fully opened, upper surface: 51B to 51C; towards the base, 145C. Fully opened, lower surface: 51B to 51C; towards the base, 143B. Spur: Length: About 2 cm. Diameter: About 1 mm. Color, upper and lower surfaces: Close to 51B to 51C.

*Pedicel.*—Length: About 9.6 cm. Diameter: About 1.5 mm. Angle: About 5 to 25° from vertical. Strength: Strong. Texture: Smooth. Color: 143A to 143B.

*Reproductive organs.*—Stamens: Quantity: About four per flower. Anther length: About 2 mm. Anther shape: Oblong. Anther color: 200C. Pollen amount: Scarce. Color: 157B. Pistils: Quantity: About five per flower. Pistil length: About 9 mm. Stigma shape: Two-parted. Stigma color: Close to N155C. Style length: About 7.5 mm. Style color: Close to 186A to 186B. Ovary color: 152C to 152D.

*Seed/fruit.*—Seed and fruit development has not been observed.

Disease/pest resistance: Plants of the new Delphinium have not been noted to be resistant to pathogens and pests common to Delphinium.

It is claimed:

1. A new and distinct cultivar of Delphinium plant named 'Coral Sunset', as illustrated and described.

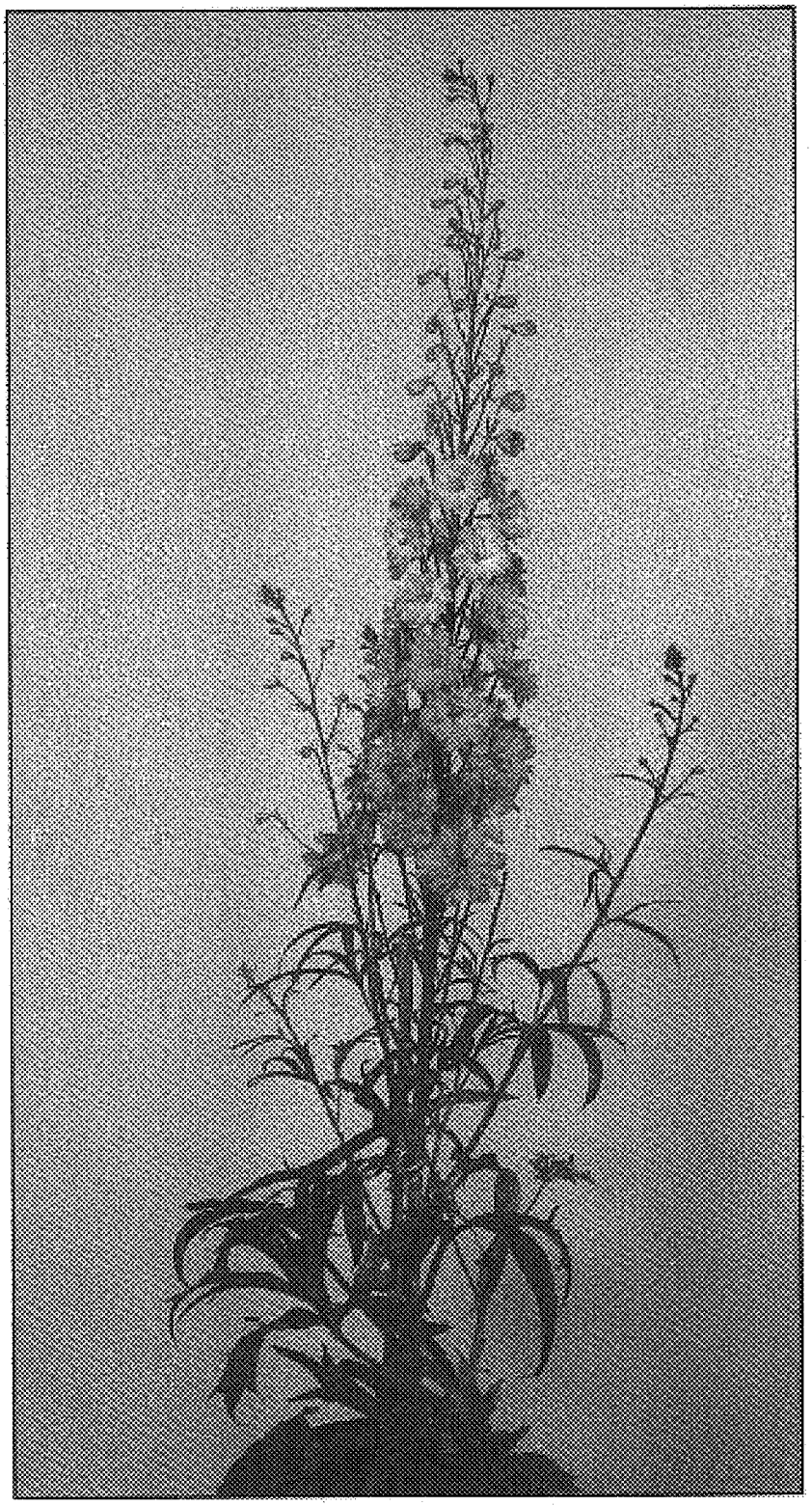

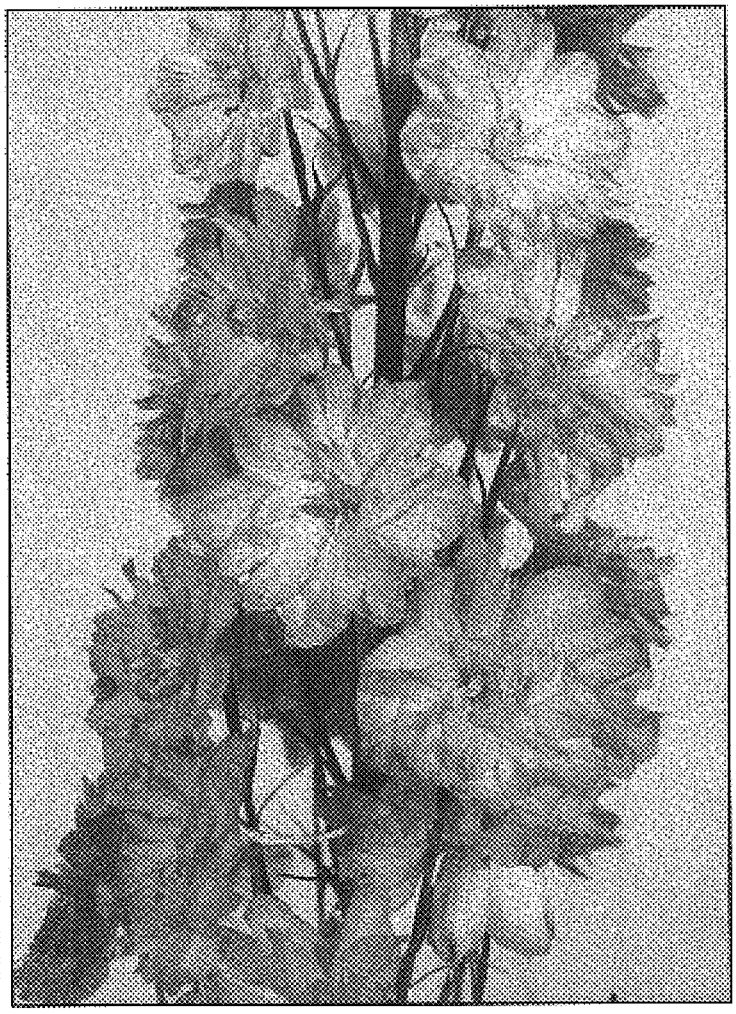
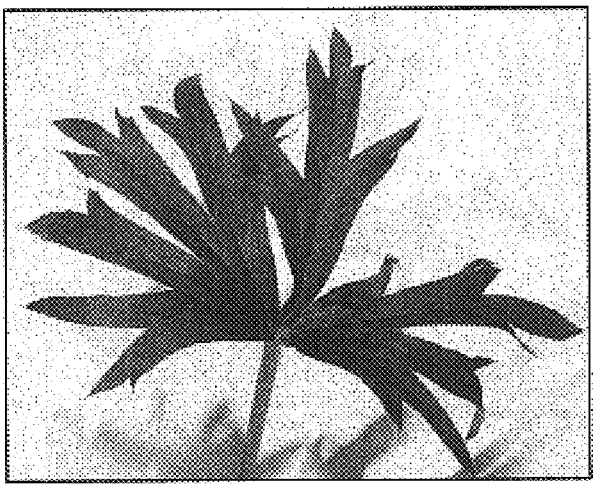

* * * * *